US010201483B2

(12) United States Patent
Charrier et al.

(10) Patent No.: US 10,201,483 B2
(45) Date of Patent: *Feb. 12, 2019

(54) DYE COMPOSITION IN CREAM FORM COMPRISING AT LEAST ONE OIL AND LITTLE OR NO SOLID FATTY ALCOHOL, DYEING PROCESS AND SUITABLE DEVICE

(71) Applicant: L'OREAL, Paris (FR)

(72) Inventors: Delphine Charrier, Boulogne Billancourt (FR); Geraldine Fack, Levallois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/418,746

(22) PCT Filed: Aug. 2, 2013

(86) PCT No.: PCT/EP2013/066263
§ 371 (c)(1),
(2) Date: Jan. 30, 2015

(87) PCT Pub. No.: WO2014/020145
PCT Pub. Date: Feb. 6, 2014

(65) Prior Publication Data
US 2015/0257994 A1    Sep. 17, 2015

Related U.S. Application Data

(60) Provisional application No. 61/698,785, filed on Sep. 10, 2012.

(30) Foreign Application Priority Data

Aug. 2, 2012   (FR) ...................... 12 57535

(51) Int. Cl.
| | |
|---|---|
| *A61Q 5/10* | (2006.01) |
| *A61K 8/41* | (2006.01) |
| *A61K 8/46* | (2006.01) |
| *A61K 8/73* | (2006.01) |
| *A61K 8/31* | (2006.01) |
| *A61K 8/34* | (2006.01) |
| *A61K 8/22* | (2006.01) |
| *A61K 8/92* | (2006.01) |

(52) U.S. Cl.
CPC .............. *A61K 8/411* (2013.01); *A61K 8/22* (2013.01); *A61K 8/31* (2013.01); *A61K 8/342* (2013.01); *A61K 8/415* (2013.01); *A61K 8/463* (2013.01); *A61K 8/737* (2013.01); *A61K 8/92* (2013.01); *A61Q 5/10* (2013.01); *A61K 2800/30* (2013.01); *A61K 2800/4324* (2013.01); *A61K 2800/542* (2013.01); *A61K 2800/882* (2013.01)

(58) Field of Classification Search
CPC .......... A61Q 5/10; A61K 8/463; A61K 8/342; A61K 8/411; A61K 8/92; A61K 8/415; A61K 8/22; A61K 2800/882; A61K 2800/4324
USPC ............................................................ 8/405
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,923,692 A | 2/1960 | Ackerman et al. |
| 2,961,347 A | 11/1960 | Floyd |
| 3,100,739 A | 8/1963 | Kaiser et al. |
| 3,206,462 A | 9/1965 | McCarty |
| 3,227,615 A | 1/1966 | Korden |
| 3,524,842 A | 8/1970 | Grossmann et al. |
| 3,578,386 A | 5/1971 | Kalopissis et al. |
| 3,589,978 A | 6/1971 | Kamal et al. |
| 3,617,163 A | 11/1971 | Kalopissis et al. |
| 3,632,559 A | 1/1972 | Matter et al. |

(Continued)

FOREIGN PATENT DOCUMENTS

| | | |
|---|---|---|
| CN | 1111444 A | 11/1995 |
| CN | 1308931 A | 8/2001 |

(Continued)

OTHER PUBLICATIONS

STIC Searech Report dated Nov. 3, 2015.*

(Continued)

*Primary Examiner* — Eisa B Elhilo
(74) *Attorney, Agent, or Firm* — The Marbury Law Group, PLLC

(57) ABSTRACT

The present invention relates to a composition for dyeing human keratin fibres, such as the hair, which is free of oxidizing agent other than atmospheric oxygen and which is in cream form, comprising: (a) at least one oxidation dye precursor; (b) at least one ionic surfactant; (c) at least one oil; (d) optionally at least one solid fatty alcohol in a content of not more than 0.5% by weight relative to the weight of the composition; (e) at least one thickening polymer. The invention also relates to a process for dyeing human keratin fibres, in which this composition is applied to the said fibres, in the presence of at least one oxidizing agent other than atmospheric oxygen, and also to a multi-compartment device that is suitable for performing this process.

16 Claims, No Drawings

(56) References Cited

U.S. PATENT DOCUMENTS

| | | |
|---|---|---|
| 3,665,036 A | 5/1972 | Kalopissis et al. |
| 3,709,437 A | 1/1973 | Wright |
| 3,817,698 A | 6/1974 | Kalopissis et al. |
| 3,867,456 A | 2/1975 | Kalopissis et al. |
| 3,869,454 A | 3/1975 | Lang et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,937,364 A | 2/1976 | Wright |
| 3,955,918 A | 5/1976 | Lang |
| 3,966,904 A | 6/1976 | Green et al. |
| 3,985,499 A | 10/1976 | Lang et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,013,787 A | 3/1977 | Varlerberghe et al. |
| 4,022,351 A | 5/1977 | Wright |
| 4,025,301 A | 5/1977 | Lang |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,117,914 A | 10/1978 | Snyder |
| 4,131,576 A | 12/1978 | Iovine et al. |
| 4,147,306 A | 4/1979 | Bennett |
| 4,151,162 A | 4/1979 | Lang et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| RE30,199 E | 1/1980 | Rose et al. |
| 4,184,615 A | 1/1980 | Wright |
| 4,189,468 A | 2/1980 | Vanlerberghe et al. |
| 4,197,865 A | 4/1980 | Jacquet et al. |
| 4,223,009 A | 9/1980 | Chakrabarti |
| 4,226,784 A | 10/1980 | Kalopissis et al. |
| 4,237,243 A | 12/1980 | Quack et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,509,949 A | 4/1985 | Huang et al. |
| 4,579,732 A | 4/1986 | Grollier et al. |
| 4,591,610 A | 5/1986 | Grollier |
| 4,598,862 A | 7/1986 | Rice |
| 4,608,250 A | 8/1986 | Jacquet et al. |
| 4,615,467 A | 10/1986 | Grogan et al. |
| 4,702,906 A | 10/1987 | Jacquet et al. |
| 4,719,282 A | 1/1988 | Nadolsky et al. |
| 4,761,273 A | 8/1988 | Grollier et al. |
| 4,777,040 A | 10/1988 | Grollier et al. |
| 4,804,385 A | 2/1989 | Grollier et al. |
| 4,886,517 A | 12/1989 | Bugaut et al. |
| 4,948,579 A | 8/1990 | Jacquet et al. |
| 4,970,066 A | 11/1990 | Grollier et al. |
| 5,061,289 A | 10/1991 | Clausen et al. |
| 5,196,189 A | 3/1993 | Jacquet et al. |
| 5,364,031 A | 11/1994 | Taniguchi et al. |
| 5,380,340 A | 1/1995 | Neunhoeffer et al. |
| 5,422,031 A | 6/1995 | Nomura et al. |
| 5,534,267 A | 7/1996 | Neunhoeffer et al. |
| 5,663,366 A | 9/1997 | Neunhoeffer et al. |
| 5,670,471 A | 9/1997 | Amalric et al. |
| 5,685,882 A | 11/1997 | Samain et al. |
| 5,708,151 A | 1/1998 | Mockli |
| 5,733,343 A | 3/1998 | Mockli |
| 5,766,576 A | 6/1998 | Lowe et al. |
| 5,879,413 A | 3/1999 | Pengilly et al. |
| 5,888,252 A | 3/1999 | Mockli |
| 5,919,273 A | 7/1999 | Rondeau et al. |
| 5,944,360 A | 8/1999 | Crapart |
| 5,993,490 A | 11/1999 | Rondeau et al. |
| 6,045,591 A | 4/2000 | Deneulenaere |
| 6,099,592 A | 8/2000 | Vidal et al. |
| 6,120,780 A | 9/2000 | Dupuis et al. |
| 6,136,042 A | 10/2000 | Maubru |
| 6,179,881 B1 | 1/2001 | Henrion et al. |
| 6,284,003 B1 | 9/2001 | Rose et al. |
| 6,338,741 B1 | 1/2002 | Vidal et al. |
| 6,458,167 B1 | 10/2002 | Genet et al. |
| 6,492,502 B2 | 12/2002 | Henrion et al. |
| 6,497,730 B1 * | 12/2002 | Genet .................. A61K 8/4973 548/311.1 |
| 6,645,258 B2 | 11/2003 | Vidal et al. |
| 6,689,922 B1 | 2/2004 | Bernardon |
| 6,730,789 B1 | 5/2004 | Birault et al. |
| 6,797,013 B1 | 9/2004 | Lang et al. |
| 6,863,883 B1 | 3/2005 | Tsujino et al. |
| 7,125,427 B2 * | 10/2006 | Schmenger ............... A61K 8/86 524/590 |
| 7,879,113 B2 | 2/2011 | Simonet et al. |
| 8,066,781 B2 | 11/2011 | Hercouet et al. |
| 8,147,564 B2 | 4/2012 | Deconinck et al. |
| 8,236,063 B2 | 8/2012 | Reichert et al. |
| 8,889,110 B2 | 11/2014 | Braida-Valerio et al. |
| 2001/0001332 A1 | 5/2001 | Henrion et al. |
| 2002/0010970 A1 | 1/2002 | Cottard et al. |
| 2002/0050013 A1 | 5/2002 | Vidal et al. |
| 2002/0165368 A1 | 11/2002 | Henrion et al. |
| 2002/0184717 A9 | 12/2002 | Cottard et al. |
| 2003/0019051 A9 | 1/2003 | Vidal et al. |
| 2004/0098815 A1 | 5/2004 | Schmenger et al. |
| 2006/0000032 A1 | 1/2006 | Knuebel et al. |
| 2006/0070191 A1 | 4/2006 | Lang et al. |
| 2006/0090269 A1 * | 5/2006 | Lagrange .................. A61K 8/49 8/405 |
| 2010/0154136 A1 | 6/2010 | Hercouet et al. |
| 2010/0158844 A1 | 6/2010 | Braida-Valerio et al. |
| 2010/0162493 A1 * | 7/2010 | Audousset ............... A61K 8/31 8/416 |
| 2010/0175202 A1 | 7/2010 | Simonet et al. |
| 2010/0223739 A1 | 9/2010 | Hercouet |
| 2010/0247465 A1 | 9/2010 | Simonet et al. |
| 2011/0033407 A1 | 2/2011 | Krueger et al. |
| 2011/0155166 A1 | 6/2011 | Deconinck et al. |
| 2012/0048288 A1 | 3/2012 | Reichert et al. |
| 2012/0276029 A1 | 11/2012 | Ascione et al. |

FOREIGN PATENT DOCUMENTS

| | | |
|---|---|---|
| CN | 101822618 A | 9/2010 |
| DE | 2359399 A1 | 6/1975 |
| DE | 2527638 A1 | 5/1976 |
| DE | 2538363 A1 | 5/1976 |
| DE | 3843892 A1 | 6/1990 |
| DE | 4133957 A1 | 4/1993 |
| DE | 4137005 A1 | 5/1993 |
| DE | 4220388 A1 | 12/1993 |
| DE | 19543988 A1 | 5/1997 |
| DE | 20114179 U1 | 10/2001 |
| DE | 102006012575 A1 | 2/2007 |
| DE | 1020090903002 A1 | 11/2010 |
| DE | 102011017519 A1 | 10/2012 |
| EP | 0080976 A1 | 6/1983 |
| EP | 0122324 A1 | 10/1984 |
| EP | 0173109 A2 | 3/1986 |
| EP | 0216479 A1 | 4/1987 |
| EP | 0395282 A2 | 10/1990 |
| EP | 0503853 A2 | 9/1992 |
| EP | 0531943 A1 | 3/1993 |
| EP | 0714954 A2 | 6/1996 |
| EP | 0770375 A1 | 5/1997 |
| EP | 0815828 A1 | 1/1998 |
| EP | 0823250 A2 | 2/1998 |

(56) References Cited

FOREIGN PATENT DOCUMENTS

| | | |
|---|---|---|
| EP | 0850636 A1 | 7/1998 |
| EP | 0850637 A1 | 7/1998 |
| EP | 0860636 A1 | 8/1998 |
| EP | 0918053 A1 | 5/1999 |
| EP | 0920856 A1 | 6/1999 |
| EP | 1062940 A1 | 12/2000 |
| EP | 1123693 A2 | 8/2001 |
| EP | 1133975 A2 | 9/2001 |
| EP | 2014275 A2 | 1/2009 |
| EP | 2198923 A2 | 6/2010 |
| EP | 2198929 A1 | 6/2010 |
| EP | 2272493 A1 | 1/2011 |
| EP | 2340807 A2 | 7/2011 |
| FR | 1221122 A | 5/1960 |
| FR | 1516943 A | 2/1968 |
| FR | 1540423 A | 8/1968 |
| FR | 1567219 A | 5/1969 |
| FR | 1583363 A | 10/1969 |
| FR | 2077143 A | 10/1971 |
| FR | 2080759 A1 | 11/1971 |
| FR | 2162025 A1 | 7/1973 |
| FR | 2189006 A1 | 1/1974 |
| FR | 2190406 A2 | 2/1974 |
| FR | 2252840 A1 | 6/1975 |
| FR | 2270846 A1 | 12/1975 |
| FR | 2275462 A1 | 1/1976 |
| FR | 2280361 A2 | 2/1976 |
| FR | 2285851 A1 | 4/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2393573 A1 | 1/1979 |
| FR | 2413907 A1 | 8/1979 |
| FR | 2416723 A1 | 9/1979 |
| FR | 2505348 A1 | 11/1982 |
| FR | 2542997 A1 | 9/1984 |
| FR | 2570946 A1 | 4/1986 |
| FR | 2722687 A1 | 1/1996 |
| FR | 1560664 A | 3/1996 |
| FR | 2733749 A1 | 11/1996 |
| FR | 2757385 A1 | 6/1998 |
| FR | 2788433 A1 | 7/2000 |
| FR | 2801308 A1 | 5/2001 |
| FR | 2886136 A1 | 12/2006 |
| FR | 2940066 A1 | 6/2010 |
| FR | 2954092 A1 | 6/2011 |
| FR | 2954095 A1 | 6/2011 |
| GB | 738585 A | 10/1955 |
| GB | 1026978 A | 4/1966 |
| GB | 1153196 A | 5/1969 |
| GB | 1163385 A | 9/1969 |
| GB | 1195386 A | 6/1970 |
| GB | 1514466 A | 6/1978 |
| GB | 1546809 A | 5/1979 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 97/44004 A1 | 11/1997 |
| WO | 98/44012 A1 | 10/1998 |
| WO | 99/36047 A1 | 7/1999 |
| WO | 99/48465 A1 | 9/1999 |
| WO | 00/26167 A1 | 5/2000 |
| WO | 01/66646 A1 | 9/2001 |
| WO | 03/020229 A2 | 3/2003 |
| WO | 03/029359 A1 | 4/2003 |
| WO | 2006/125619 A1 | 11/2006 |
| WO | 2008/049768 A1 | 5/2008 |
| WO | 2010/133640 A2 | 11/2010 |
| WO | 2011/009563 A2 | 1/2011 |
| WO | 2014/020146 A2 | 2/2014 |
| WO | 2014/020147 A1 | 2/2014 |
| WO | 2014/020148 A2 | 2/2014 |
| WO | 2014108433 A1 | 7/2014 |

OTHER PUBLICATIONS

International Search Report and Written Opinion for PCT/EP2013/066268, dated Sep. 25, 2013.
International Search Report and Written Opinion for co-pending PCT/EP2013/066266 (WO 2014/020147A2), dated May 15, 2014.
International Search Report for co-pending PCT/EP2013/066263 (WO 2014/020145A2), dated Oct. 18, 2013.
International Search Report and Written Opinion for co-pending PCT/EP2013/066264 (WO 2014/020146A2), dated Nov. 4, 2014.
English language abstract for DE 4137005A1 (May 13, 1993).
English language Abstract for DE 4220388A1 (Dec. 23, 1993).
English language Abstract for DE 102006012575A1. (Feb. 8, 2007).
English language Abstract for EP 0080976A1 (Jun. 8, 1983).
English language Abstract for EP 0770375A1 (May 2, 1997).
English language Abstract for EP 1123693A2 (Aug. 16, 2001).
English language Abstract for EP 2014276A2 (Jan. 14, 2009).
English language Abstract for FR 2886136A1 (EP1728500) (Dec. 1, 2006).
English language Abstract for FR 2940066A1 (Jun. 25, 2010).
English language Abstract for JP 02-019576A (Jan. 23, 1990).
English language Abstract for JP 05-163124A (Jun. 29, 1993).
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
International Search Report for counterpart foreign Application PCT/EP2014/0502110, dated May 20, 2014.
Non-Final Office Action for co-pending U.S. Appl. No. 14/418,699, dated Feb. 18, 2016.
Non-Final Office Action for co-pending U.S. Appl. No. 14/418,736, dated Nov. 20, 2015.
Final Office Action for co-pending U.S. Appl. No. 14/418,736, dated Jun. 2, 2016.
Non-Final Office Action for co-pending U.S. Appl. No. 14/418,762, dated Nov. 17, 2015.
Non-Final Office Action for co-pending U.S. Appl. No. 14/758,985, dated Jan. 22, 2016.
Final Office Action for co-pending U.S. Appl. No. 14/418,762, dated Jul. 18, 2016.
Machine translation of First Office Action for counterpart Chinese Application 201380040848.0, dated Feb. 29, 2016.
Machine translation of Second Office Action for counterpart Chinese Application 201380040848.0, dated Nov. 22, 2016.
Machine translation of First Office Action for counterpart Chinese Application 201380040807.1, dated Feb. 2, 2016.
Machine translation of Second Office Action for counterpart Chinese Application 201380040807.1, dated Dec. 16, 2016.
Non-Final Office Action for copending U.S. Appl. No. 14/418,736, dated Dec. 14, 2016.
Final Office Action for copending U.S. Appl. No. 14/418,699, dated Sep. 8, 2016.
Non-Final Office Action for copending U.S. Appl. No. 14/418,762, dated Feb. 7, 2017.
Final Office Action for copending U.S. Appl. No. 14/758,985, dated Jul. 26, 2016.
Non-Final Office Action for copending U.S. Appl. No. 14/758,985, dated Feb. 15, 2017.
Non-Final Office Action for copending U.S. Appl. No. 14/418,699, dated Aug. 16, 2017.
Final Office Action for copending U.S. Appl. No. 14/418,736, dated Jul. 12, 2017.
Non-Final Office Action for copending U.S. Appl. No. 14/418,736, dated Jan. 29, 2018.
Final Office Action for copending U.S. Appl. No. 14/758,985, dated Sep. 14, 2017.
Non-Final Office Action for copending U.S. Appl. No. 14/758,985, dated Apr. 12, 2018.

(56) References Cited

OTHER PUBLICATIONS

Final Office Action for copending U.S. Appl. No. 14/418,736, dated Jul. 18, 2018.
Notice of Allowance for copending U.S. Appl. No. 14/418,699, dated Jul. 26, 2018.
Final Office Action for copending U.S. Appl. No. 14/758,985, dated Jul. 24, 2018.

* cited by examiner

DYE COMPOSITION IN CREAM FORM COMPRISING AT LEAST ONE OIL AND LITTLE OR NO SOLID FATTY ALCOHOL, DYEING PROCESS AND SUITABLE DEVICE

This is a national stage application of PCT/EP2013/066263, filed internationally on Aug. 2, 2013, which claims priority to U.S. Provisional Application No. 61/698,785, filed on Sep. 10, 2012; as well as French Application 1257535, filed on Aug. 2, 2012.

The present invention relates to a dye composition free of oxidizing agent other than atmospheric oxygen, in the form of a cream, comprising oxidation dye precursors, at least a first surfactant, at least one oil, not more than 0.5% by weight of at least one solid fatty alcohol, and at least one thickener, and also to a dyeing process using the said composition in the presence of an oxidizing agent other than atmospheric oxygen. The present invention also relates to a suitable multi-compartment device.

Among the methods for dyeing human keratin fibres, such as the hair, mention may be made of oxidation dyeing or permanent dyeing. More particularly, this form of dyeing uses one or more oxidation dyes, usually one or more oxidation bases optionally combined with one or more couplers.

In general, the oxidation bases are chosen from ortho- or para-phenylenediamines, ortho or para-aminophenols and heterocyclic compounds. These oxidation bases are colourless or weakly coloured compounds, which, when combined with oxidizing products, can give access to coloured species.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

Permanent dyeing processes thus consist in using, with the dye composition containing the oxidation dyes, an aqueous composition comprising at least one oxidizing agent such as hydrogen peroxide, under alkaline pH conditions in the vast majority of cases. The alkaline agent conventionally used is aqueous ammonia or it may be chosen from other alkaline agents, such as alkanolamines.

Recently, dyeing formulations comprising fatty substance contents higher than the compositions thus far on the market have been developed. These formulations provide numerous advantages, in particular inasmuch as they make it possible to reduce the aqueous ammonia content, thus providing a very clear improvement in the user's comfort (less of an unpleasant smell and less risk of stinging), without any decrease in the dyeing performance qualities being observed, or even with them being increased.

However, such formulations are complex to use on account, precisely, of this high content of fatty substances and, for example, as regards the ease of mixing with the oxidizing composition. The mixtures may take longer to produce and may require higher forces.

They may also lead to a deterioration of the working qualities such as the ease of application and the rinseability.

The object of the present invention is thus to improve the mixability of dye compositions with the oxidizing composition, and also the working qualities of dye compositions that are in cream form, comprising high contents of fatty substances, without causing any reduction in the dyeing performance qualities of such compositions.

This aim and others are achieved by the present invention, one subject of which is thus a composition for dyeing human keratin fibres, such as the hair, which is free of oxidizing agent other than atmospheric oxygen and which is in cream form, comprising:
(a) at least one oxidation dye precursor;
(b) at least one ionic surfactant;
(c) at least one oil;
(d) optionally at least one solid fatty alcohol in a content of not more than 0.5% by weight relative to the weight of the composition;
(e) at least one thickening polymer.

A subject of the invention is also a dyeing process in which such a composition is used, in the presence of an oxidizing agent other than atmospheric oxygen.

Finally, the invention relates to a multi-compartment device comprising a compartment containing a composition free of oxidizing agent other than atmospheric oxygen, comprising at least one oxidation dye precursor; at least one ionic surfactant; at least one oil; optionally at least one solid fatty alcohol in a content of not more than 0.5% by weight relative to the weight of the composition; at least one thickening polymer; and a compartment containing an oxidizing composition.

The composition of the invention makes it possible to obtain good dyeing properties, such as strength of the colour, resistance to external agents (shampooing, perspiration, light) and homogeneity, which are particularly efficient.

It also has a texture suitable for the application. Specifically, the composition according to the invention is easy to mix with the oxidizing composition and easy to apply to the fibres. Similarly, it rinses off easily after the leave-on time.

Other characteristics and advantages of the invention will emerge more clearly on reading the description and the examples that follow.

In the text hereinbelow, and unless otherwise indicated, the limits of a range of values are included in that range.

The term "at least one" associated with an ingredient of the composition signifies "one or more".

The human keratin fibres treated by means of the process according to the invention are preferably the hair.

The composition is in the form of a cream. Thus, the composition has a viscosity of at least 5 poises measured at 25° C. using a Rheomat 180 viscometer and at a shear rate of 60 $s^{-1}$. Preferably, the viscosity may range from 5 poises to 500 poises, more particularly from 7 poises to 250 poises and preferably from 8 poises to 100 poises.

Dyes

As indicated previously, the dyeing composition according to the invention comprises at least one oxidation dye precursor.

As oxidation dye precursors, use may be made of oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Mention may be made, among bis(phenyl)alkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, mention may be made, by way of example, of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases of use in the present invention are the 3-aminopyrazolo[1,5-a]pyridine oxidation bases or addition salts thereof described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, and the addition salts thereof.

Mention may be made, among pyrimidine derivatives, of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned, for example, are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl) pyrazole and/or a salt thereof.

Mention may also be made, as pyrazole derivatives, of diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3- dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one. Use is preferably made of 2,3-diamino-6,7-dihydro-1H,5H-pyrazolo[1,2-a]pyrazol-1-one and/or a salt thereof.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or a salt thereof.

Among the couplers that may be used in the composition according to the invention, mention may be made in particular of meta-phenylenediamines, meta-aminophenols, meta-diphenols, naphthalene-based couplers, heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts of these compounds with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, the addition salts thereof with an acid, and mixtures thereof.

The addition salts of the oxidation bases and couplers are in particular chosen from the addition salts with an acid, such as the hydrochlorides, hydrobromides, sulfates, citrates, succinates, tartrates, lactates, tosylates, benzenesulfonates, phosphates and acetates.

The oxidation base(s) are generally each present in an amount from 0.0001% to 10% by weight relative to the total weight of the composition of the invention, and preferably from 0.005% to 5% by weight relative to the total weight of the composition.

The coupler(s) each generally represent from 0.0001% to 10% by weight relative to the total weight of the composition and preferably from 0.005% to 5% by weight relative to the total weight of the composition of the invention.

The composition used in the process according to the invention may optionally comprise synthetic or natural, cationic or nonionic, direct dyes.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures. In particular, mention may be made of direct dyes from among: azo; methine; carbonyl; azine; nitro (hetero)aryl; tri(hetero)arylmethane; porphyrin; phthalocyanine and natural direct dyes, alone or as mixtures.

When they are present, the direct dye(s) more particularly represent from 0.0001% to 10% by weight of the total weight of the dye composition and preferably from 0.005% to 5% by weight.

Surfactants

The dye composition according to the invention also comprises at least one ionic surfactant. This ionic surfactant may preferably be chosen from anionic, amphoteric or zwitterionic surfactants, or mixtures thereof.

Amphoteric or Zwitterionic Surfactants

In particular, the amphoteric or zwitterionic surfactant(s), which are preferably non-silicone, which are usable in the present invention may especially be derivatives of optionally quaternized aliphatic secondary or tertiary amines, in which derivatives the aliphatic group is a linear or branched chain comprising from 8 to 22 carbon atoms, the said amine derivatives containing at least one anionic group, for instance a carboxylate, sulfonate, sulfate, phosphate or phosphonate group.

Mention may be made in particular of ($C_8$-$C_{20}$)alkylbetaines, ($C_8$-$C_{20}$)alkylsulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized secondary or tertiary aliphatic amine derivatives that can be used, as defined above, mention may also be made of the compounds of respective structures (B1) and (B2) below:

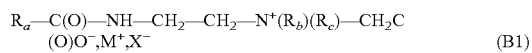

(B1)

in which formula:
$R_a$ represents a $C_{10}$-$C_{30}$ alkyl or alkenyl group derived from an acid $R_a$—COOH preferably present in hydrolysed coconut oil, or a heptyl, nonyl or undecyl group;
$R_b$ represents a β-hydroxyethyl group; and
$R_c$ represents a carboxymethyl group;
$M^+$ represents a cationic counterion derived from an alkali metal or alkaline-earth metal, such as sodium, an ammonium ion or an ion derived from an organic amine, and
$X^-$ represents an organic or mineral anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate; or alternatively $M^+$ and $X^-$ are absent;

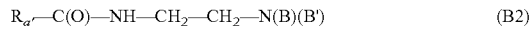

(B2)

in which formula:
B represents the group —CH$_2$—CH$_2$—O—X';
B' represents the group —(CH$_2$)$_z$Y', with z=1 or 2;
X' represents the group —CH$_2$—C(O)OH, —CH$_2$—C(O)OZ', —CH$_2$—CH$_2$—C(O)OH, —CH$_2$—CH$_2$—C(O)OZ', or a hydrogen atom;
Y' represents the group —C(O)OH, —C(O)OZ', —CH$_2$—CH(OH)—SO$_3$H or the group —CH$_2$—CH(OH)—SO$_3$—Z';
Z' represents a cationic counterion derived from an alkali metal or alkaline-earth metal, such as sodium, an ammonium ion or an ion derived from an organic amine;
$R_{a'}$ represents a $C_{10}$-$C_{30}$ alkyl or alkenyl group of an acid $R_{a'}$—C(O)OH preferably present in hydrolysed linseed oil or coconut oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® $C_2M$ Concentrate.

Use may also be made of compounds of formula (B'2):

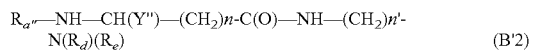

(B'2)

in which formula:
Y" represents the group —C(O)OH, —C(O)OZ", —CH$_2$—CH(OH)—SO$_3$H or the group —CH$_2$—CH(OH)—SO$_3$—Z"

$R_d$ and $R_e$ represent, independently of each other, a $C_1$-$C_4$ alkyl or hydroxyalkyl radical;

Z" represents a cationic counterion derived from an alkali metal or alkaline-earth metal, such as sodium, an ammonium ion or an ion derived from an organic amine;

$R_{a''}$ represents a $C_{10}$-$C_{30}$ alkyl or alkenyl group of an acid $R_{a''}$—C(O)OH preferably present in hydrolysed linseed oil or coconut oil;

n and n' denote, independently of each other, an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of ($C_8$-$C_{20}$)alkylbetaines such as cocoylbetaine, ($C_8$-$C_{20}$)alkylamido($C_3$-$C_8$) alkylbetaines such as cocamidopropylbetaine, and mixtures thereof, and the compounds of formula (B'2), such as the sodium salt of diethylaminopropyl laurylaminosuccinamate (INCI name: sodium diethylaminopropyl cocoaspartamide).

More preferentially, the amphoteric or zwitterionic surfactant(s) are chosen from cocamidopropylbetaine and cocoylbetaine, the sodium salt of diethylaminopropyl laurylaminosuccinamate, or mixtures thereof.

Anionic Surfactants

The term "anionic surfactant" is intended to mean a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH) O$^-$, =P(O)O$^-$, =POH and =PO$^-$, the anionic parts comprising a cationic counterion such as an alkali metal, an alkaline-earth metal or an ammonium.

By way of examples of anionic surfactants that may be used in the dye composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N-acyltaurates, salts of alkyl monoesters of polyglycoside-polycarboxylic acids, acyllactylates, D-galactoside uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, it/they may be chosen from alkali metal salts such as the sodium or potassium salt and preferably the sodium salt, ammonium salts, amine salts and in particular amino alcohol salts or alkaline-earth metal salts such as the magnesium salts.

By way of examples of amino alcohol salts, mention may in particular be made of monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Use is preferably made, among the additional anionic surfactants mentioned, of ($C_6$-$C_{24}$)alkyl sulfates, ($C_6$-$C_{24}$) alkyl ether sulfates comprising from 2 to 50 ethylene oxide units, in particular in the form of alkali metal, ammonium, amino alcohol and alkaline-earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

The composition of the invention may comprise, in addition to the ionic surfactant, at least one nonionic surfactant.

Nonionic Surfactants

Examples of nonionic surfactants that may be used in the dye composition used according to the invention are described, for example, in the *Handbook of Surfactants* by M. R. Porter, published by Blackie & Son (Glasgow and London), 1991, pp. 116-178.

Examples of nonionic additional surfactants that may be mentioned include oxyalkylenated, or glycerolated, nonionic surfactants, in particular the following surfactants, alone or as mixtures:

oxyalkylenated ($C_8$-$C_{24}$)alkylphenols;
saturated or unsaturated, linear or branched, oxyalkylenated or glycerolated $C_8$-$C_{30}$ alcohols;
saturated or unsaturated, linear or branched, oxyalkylenated $C_8$-$C_{30}$ fatty acid amides; saturated or unsaturated, linear or branched, $C_8$-$C_{30}$ acid esters of polyethylene glycols;
saturated or unsaturated, linear or branched, $C_8$-$C_{30}$ acid esters of sorbitol, which are preferably oxyethylenated;
fatty acid esters of sucrose;
($C_8$-$C_{30}$)alkylpolyglycosides, ($C_8$-$C_{30}$)alkenylpolyglycosides, which are optionally oxyalkylenated (0 to 10 oxyalkylene units) and which comprise 1 to 15 glucose units, ($C_8$-$C_{30}$)alkylglucoside esters;
saturated or unsaturated, oxyethylenated plant oils;
condensates of ethylene oxide and/or of propylene oxide, inter alia, alone or as mixtures;
N—($C_8$-$C_{30}$)alkylglucamine derivatives and N—($C_8$-$C_{30}$)acyl-methylglucamine derivatives;

aldobionamides;
amine oxides;
oxyethylenated and/or oxypropylenated silicones.

The oxyalkylene units are more particularly oxyethylene or oxypropylene units, or a combination thereof, preferably oxyethylene units.

The number of moles of ethylene oxide and/or of propylene oxide preferably ranges from 1 to 100, more particularly from 2 to 50; the number of moles of glycerol ranges in particular from 1 to 30.

Advantageously, the nonionic surfactants do not comprise oxypropylene units.

By way of example of glycerolated nonionic surfactants, use may preferably be made of monoglycerolated or polyglycerolated $C_8$-$C_{40}$ alcohols comprising from 1 to 30 mol of glycerol, preferably from 1 to 10 mol of glycerol.

Examples of compounds of this type that may be mentioned include lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the glycerolated alcohols, it is more particularly preferred to use $C_8/C_{10}$ alcohol containing 1 mol of glycerol, $C_{10}/C_{12}$ alcohol containing 1 mol of glycerol and $C_{12}$ alcohol containing 1.5 mol of glycerol.

In accordance with a preferred embodiment of the invention, the nonionic surfactant(s) are chosen from:
  oxyethylenated $C_8$-$C_{30}$ alcohols comprising from 1 to 100 mol of ethylene oxide, preferably from 2 to 50, and more particularly from 2 to 30 mol of ethylene oxide;
  saturated or unsaturated, oxyethylenated plant oils comprising from 1 to 100 mol of ethylene oxide, preferably from 2 to 50;
  ($C_8$-$C_{30}$)alkylpolyglycosides, which are optionally oxyalkylenated (0 to 10 oxyalkylene and preferably oxyethylene units) and which comprise 1 to 15 glucose units;
  monoglycerolated or polyglycerolated $C_8$-$C_{40}$ alcohols comprising from 1 to 30 mol of glycerol, preferably from 1 to 10 mol of glycerol;
  saturated or unsaturated, linear or branched, oxyalkylenated $C_8$-$C_{30}$ fatty acid amides;
  and mixtures thereof.

In a first variant of the invention, the composition of the invention comprises at least one anionic surfactant. In this variant, the use of anionic surfactants of alkyl sulfate or alkyl ether sulfate type is preferred.

In a second variant of the invention, the composition of the invention comprises at least one nonionic surfactant even more preferentially chosen from saturated or unsaturated, linear or branched $C_8$-$C_{30}$ acid esters of sorbitol, which are preferably oxyethylenated.

According to a particular embodiment of the invention, the content of ionic surfactant(s) ranges from 0.1% to 15% by weight, preferably from 0.5% to 10% by weight and more preferably from 1% to 5% by weight, relative to the total weight of the composition.

According to a particular embodiment of the invention, the content of surfactant(s) ranges from 0.1% to 30% by weight, preferably from 0.5% to 20% by weight and more preferably from 1% to 10% by weight, relative to the total weight of the composition.

The Oils

The composition of the invention comprises at least one oil. The emulsion (A) may contain one or more oils of different nature.

The term "oil" means a "fatty substance" that is liquid, i.e. that is capable of flowing under the action of its own weight at room temperature (25° C.) and at atmospheric pressure ($10^5$ Pa).

Preferably, the viscosity at a temperature of 25° C. and at a shear rate of 1 s$^{-1}$ of the oil is between $10^{-3}$ Pa·s and 2 Pa·s. It may be measured using a Thermo Haake RS600 rheometer with cone-plate geometry or an equivalent machine.

The term "fatty substance" means an organic compound that is insoluble in water at room temperature (25° C.) and at atmospheric pressure (760 mmHg) (solubility of less than 5%, preferably 1% and even more preferentially 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, ethanol, benzene, liquid petrolatum or decamethylcyclopentasiloxane.

The oils of the invention do not contain any salified carboxylic acid groups.

In addition, the oils of the invention are not (poly)oxyalkylenated or (poly)glycerolated ethers.

Among the oils, mention may be made of:
  halogenated or non-halogenated linear or branched hydrocarbons, of mineral or synthetic origin, containing less than 16 carbon atoms, for instance hexane, cyclohexane, undecane, dodecane, isododecane, tridecane or perfluorohexane, or more than 16 carbon atoms, such as liquid petroleum jelly;
  unsaturated or branched liquid fatty alcohols comprising from 6 to 30 carbon atoms, such as those of formula $C_nH_{2n+1}OH$ with n being an integer between 6 and 20 inclusive. Mention may be made especially of oleyl alcohol, linolenyl alcohol, linoleyl alcohol, ricinoleyl alcohol, undecylenyl alcohol, isostearyl alcohol and octyldodecanol.
  triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil; and
  liquid esters other than triglycerides.

These esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one of the alcohol or of the acid from which the esters of the invention result is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates and arachidonates, or mixtures thereof, such as, in particular, oleopalmitate, oleostearate or palmitostearate mixed esters.

More particularly, use is made of monoesters and diesters and in particular of sucrose, glucose or methylglucose mono- or dioleates, stearates, behenates, oleopalmitates, linoleates, linolenates or oleostearates.

An example that may be mentioned is the product sold under the name Glucate® DO by the company Amerchol, which is a methylglucose dioleate.

The oil may be a fluoro oil, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052® by the company 3M.

The oil according to the invention may also be a liquid silicone oil.

The term "liquid silicone" means an organopolysiloxane that is liquid at ordinary temperature (25° C.) and at atmospheric pressure (760 mmHg; i.e. $1.013 \times 10^5$ Pa).

Preferably, the silicone is chosen from liquid polydialkylsiloxanes, in particular liquid polydimethylsiloxanes (PDMSs), and liquid polyorganosiloxanes comprising at least one aryl group.

These silicones may also be organomodified. The organomodified silicones that may be used in accordance with the invention are liquid silicones as defined previously, comprising in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide or Silbione® 70045 V5 by Rhodia, and dodecamethylcyclopentasiloxane sold under the name Silsoft 1217 by Momentive Performance Materials, and mixtures thereof.

Mention may also be made of cyclocopolymers of the dimethylsiloxane/methylalkylsiloxane type, such as Volatile Silicone® FZ 3109 sold by the company Union Carbide, of formula:

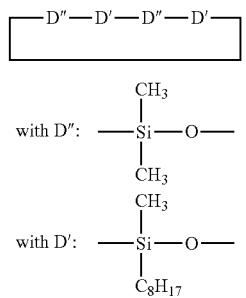

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone.

Silicones falling within this category are also described in the article published in Cosmetics and Toiletries, Vol. 91, January 76, pp. 27-32, Todd & Byers *Volatile Silicone Fluids*

*for Cosmetics*. The viscosity of the silicones is measured at 25° C. according to Standard ASTM 445 Appendix C.

Non-volatile polydialkylsiloxanes may also be used.

These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, such as, for example, the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of series 48 from the company Rhodia.

Among the silicones containing aryl groups are polydiarylsiloxanes, in particular polydiphenylsiloxanes and polyalkylarylsiloxanes. Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

According to a preferred variant, the oil(s) are chosen from $C_6$-$C_{16}$ lower alkanes; glycerides of plant or synthetic origin; linear or branched hydrocarbons of mineral or synthetic origin containing more than 16 carbon atoms; liquid fatty alcohols; liquid fatty esters; or mixtures thereof.

Even more preferentially, the oil(s) are chosen from $C_6$-$C_{16}$ lower alkanes; linear or branched hydrocarbons of mineral or synthetic origin containing more than 16 carbon atoms; liquid fatty alcohols; or mixtures thereof.

Preferably, the oil(s) are chosen from mineral oils such as liquid petroleum jelly, polydecenes, octyldodecanol and isostearyl alcohol, or mixtures thereof.

Preferably, the oil is chosen from isododecane and mineral oils, such as liquid petroleum jelly.

The composition according to the invention more particularly comprises at least 10% by weight of oil(s), and even more preferentially at least 15% by weight, even more advantageously at least 20% by weight, better still at least 25% by weight, even better still at least 30% by weight and up to 70% by weight of oil(s), relative to the total weight of the composition.

Solid Fatty Alcohols

As indicated previously, the composition according to the invention optionally comprises at least one fatty alcohol that is solid at room temperature (25° C., 760 mmHg); its contents, if it is present, being between 0 exclusive and 0.5% by weight relative to the weight of the composition.

The fatty alcohols that are solid at room temperature are more particularly chosen from linear or branched, saturated or unsaturated alcohols comprising from 8 to 30 carbon atoms. Preferably, the fatty alcohol(s) are chosen from saturated, linear fatty alcohols containing from 8 to 30 and preferably from 10 to 22 carbon atoms. In addition, it is understood that the fatty alcohols do not comprise any oxyalkylenated $C_2$-$C_3$ unit(s) or any glycerolated unit(s). Examples that may be mentioned include cetyl alcohol, stearyl alcohol and behenyl alcohol, and mixtures thereof (cetylstearyl alcohol).

Preferably, the composition according to the invention does not comprise any solid fatty alcohol.

Other Additional Fatty Substances

The composition according to the invention may comprise, besides the oils and the solid fatty alcohols, other solid fatty substances.

These additional solid fatty substances may in particular be esters and ceramides, in particular ceramides.

Preferably, if they are present, these additional fatty substances other than the oils and the solid fatty alcohols represent less than 0.5% by weight relative to the weight of the composition.

Thickening Polymer

The composition also comprises at least one thickening polymer.

This thickening polymer is chosen from ionic and nonionic non-associative polymers, or from nonionic, anionic, cationic and amphoteric associative polymers, and also mixtures thereof.

For the purpose of the present invention, the term "thickening polymer" means a polymer which, when introduced at 1% in a pure aqueous solution or an aqueous-alcoholic solution containing 30% ethanol, and at pH 7, makes it possible to achieve a viscosity of at least 100 cps and preferably of at least 500 cps, at 25° C. and at a shear rate of 1 s$^{-1}$. This viscosity may be measured using a cone/plate viscometer (Haake R600 rheometer or the like).

Preferably, these polymers increase, by virtue of their presence, the viscosity of the compositions into which they are introduced by at least 50 cps and preferably 200 cps, at 25° C. and a shear rate of 1 s$^{-1}$.

Non-Associative Polymers

As regards the non-associative thickening polymers, it is first recalled that, for the purposes of the present invention, non-associative thickening polymers are thickening polymers not containing any $C_8$-$C_{30}$ fatty chains.

Among the non-associative thickening polymers present, mention may be made of:

a) crosslinked homopolymers or copolymers of acrylic or methacrylic acid,
b) crosslinked homopolymers of 2-acrylamido-2-methylpropanesulfonic acid, and crosslinked acrylamide copolymers thereof,
c) ammonium acrylate homopolymers or copolymers of ammonium acrylate and of acrylamide,
d) nonionic guar gums,
e) biopolysaccharide gums of microbial origin, gums derived from plant exudates,
f) celluloses, in particular hydroxypropyl- or carboxymethyl-celluloses,
g) pectins and alginates,
h) mixtures thereof.

A first family of suitable non-associative thickening polymers is represented by crosslinked acrylic acid homopolymers, such as those crosslinked with an allyl ether of an alcohol from the sugar series, for instance the products sold under the names Carbopol 980, 981, 954, 2984 and 5984 by the company Noveon or the products sold under the names Synthalen M and Synthalen K by the company 3 VSA.

The nonassociative thickening polymers may also be crosslinked (meth)acrylic acid copolymers, such as the polymer sold under the name Aqua SF1 by the company Noveon.

The nonassociative thickening polymers may be chosen from crosslinked 2-acrylamido-2-methylpropanesulfonic acid homopolymers and the crosslinked acrylamide copolymers thereof.

As regards these homopolymers and copolymers, which may be partially or totally neutralized, mention may be made of polymers comprising from 90% to 99.9% by weight, relative to the total weight of the polymer, of units of formula (j) below:

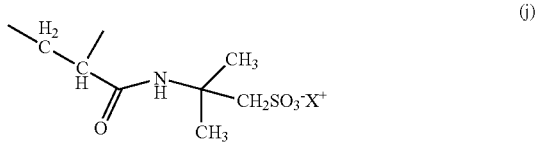

in which $X^+$ denotes a cation or a mixture of cations, or a proton.

More particularly, the cations are chosen from alkali metals (for instance sodium or potassium), ammonium ions optionally substituted with 1 to 3 alkyl radicals, which may be identical or different, containing from 1 to 6 carbon atoms, optionally bearing at least one hydroxyl radical, cations derived from N-methylglucamine or from basic amino acids, for instance arginine and lysine. Preferably, the cation is an ammonium or sodium ion.

Moreover, the polymer comprises from 0.01% to 10% by weight, relative to the total weight of the polymer, of crosslinking units derived from at least one monomer containing at least two ethylenic unsaturations (carbon-carbon double bond).

The crosslinking monomers containing at least two ethylenic unsaturations are chosen, for example, from diallyl ether, triallyl cyanurate, diallyl maleate, allyl(meth)acrylate, dipropylene glycol diallyl ether, polyglycol diallyl ethers, triethylene glycol divinyl ether, hydroquinone diallyl ether, tetraallyloxyethane, tetra- or diethylene glycol di(meth)acrylate, triallylamine, tetraallylethylenediamine, trimethylolpropane diallyl ether, trimethylolpropane triacrylate, methylenebis(meth)acrylamide or divinylbenzene, allylic ethers of alcohols of the sugar series, or other allylic or vinyl ethers of polyfunctional alcohols, and also allylic esters of phosphoric and/or vinylphosphonic acid derivatives, or mixtures of these compounds.

For further details regarding these polymers, reference may be made to document EP 815 828.

Among the partially or totally neutralized crosslinked copolymers of 2-acrylamido-2-methylpropanesulfonic acid and of acrylamide, mention may be made in particular of the product described in Example 1 of document EP 503 853, and reference may be made to said document as regards these polymers.

The composition may similarly comprise, as nonassociative thickening polymers, ammonium acrylate homopolymers or copolymers of ammonium acrylate and of acrylamide.

Among the ammonium acrylate homopolymers that may be mentioned is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made especially to documents FR 2 416 723, U.S. Pat. No. 2,798,053 and U.S. Pat. No. 2,923,692 as regards the description and preparation of such compounds.

The composition may also comprise dimethylaminoethyl methacrylate homopolymers quaternized with methyl chloride or dimethylaminoethyl methacrylate copolymers quaternized with methyl chloride and acrylamide.

Among the homopolymers of this type, mention may be made of the products sold under the names Salcare SC95 and Salcare SC96 by the company Ciba. Among the copolymers of this family, mention may be made of the product Salcare SC92 sold by Ciba or the product PAS 5194 sold by Hoechst. These polymers are especially described and prepared in document EP 395 282, to which reference may be made.

Non-associative thickening polymers that may be mentioned include nonionic guar gums, for instance the unmodified nonionic guar gums sold under the name Vidogum GH 175 by the company Unipectine and under the name Jaguar C by the company Meyhall.

The nonionic guar gums that may be used according to the invention are preferably modified with $C_1$-$C_6$ hydroxyalkyl groups. Among the hydroxyalkyl groups that may be mentioned, for example, are hydroxymethyl, hydroxyethyl, hydroxypropyl and hydroxybutyl groups.

These guar gums are well known in the prior art and may be prepared, for example, by reacting the corresponding alkene oxides, for instance propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall or under the name Galactasol 4H4FD2 by the company Aqualon.

Suitable non-associative thickening polymers that may also be mentioned include biopolysaccharide gums of microbial origin such as scleroglucan gum or xanthan gum.

Gums that are also suitable for use are those derived from plant exudates, such as gum arabic, ghatti gum, karaya gum and gum tragacanth; celluloses, in particular hydroxypropyl- or carboxymethyl-celluloses; pectins and alginates.

These polymers are well known to those skilled in the art and are especially described in the book by Robert L. Davidson entitled *Handbook of water-soluble gums and resins* published by the McGraw-Hill Book Company (1980).

Associative Polymers

It is recalled that associative polymers are hydrophilic polymers that are capable, in an aqueous medium, of reversibly associating with each other or with other molecules.

Their chemical structure more particularly comprises at least one hydrophilic region and at least one hydrophobic region.

The term "hydrophobic group" means a radical or polymer with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative polymers that are suitable for use in the invention, mention may be made of:

a) Anionic associative polymers comprising at least one hydrophilic unit of the type such as an ethylenic unsaturated anionic monomer, in particular a vinyl carboxylic acid, and most particularly an acrylic acid or a methacrylic acid or mixtures thereof, and at least one fatty-chain allyl ether unit comprising from 8 to 30 carbon atoms, corresponding especially to the monomer of formula (I) below:

$$CH_2=CR'CH_2OB_nR \qquad (I)$$

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10, and R denotes a stearyl radical ($C_{18}$).

Anionic associative polymers of this type are described and prepared, according to an emulsion polymerization process, in patent EP-0 216 479.

Among these anionic associative polymers, those that are particularly preferred according to the invention are polymers formed from 20% to 60% by weight of acrylic acid and/or of methacrylic acid, from 5% to 60% by weight of lower alkyl(meth)acrylates, from 2% to 50% by weight of fatty-chain allyl ether of formula (I), and from 0 to 1% by weight of a crosslinking agent which is a well-known copolymerizable unsaturated polyethylenic monomer, for instance diallyl phthalate, allyl(meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

b) anionic associative polymers comprising at least one hydrophilic unit of unsaturated olefinic carboxylic acid type and at least one hydrophobic unit of the type such as a ($C_{10}$-$C_{30}$)alkyl ester of an unsaturated carboxylic acid.

These polymers are preferably chosen from those in which the hydrophilic unit of unsaturated olefinic carboxylic acid type corresponds to the monomer having the following formula (II):

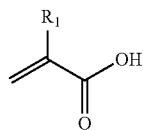

(II)

in which $R_1$ denotes H or $CH_3$ or $C_5H5$, i.e. acrylic acid, methacrylic acid or ethacrylic acid units, and of which the hydrophobic unit of the type such as a ($C_{10}$-$C_{30}$)alkyl ester of an unsaturated carboxylic acid corresponds to the monomer having the following formula (III):

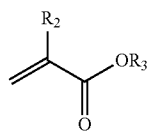

(III)

in which $R_2$ denotes H or $CH_3$ or $C_2H5$ (i.e. acrylate, methacrylate or ethacrylate units) and preferably H (acrylate units) or $CH_3$ (methacrylate units), $R_3$ denoting a $C_{10}$-$C_{30}$ and preferably $C_{12}$-$C_{22}$ alkyl radical.

($C_{10}$-$C_{30}$)alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to patents U.S. Pat. No. 3,915,921 and U.S. Pat. No. 4,509,949.

Among anionic associative polymers of this type that will be used more particularly are polymers formed from a monomer mixture comprising:
  essentially acrylic acid,
  an ester of formula (III) described above in which $R_2$ denotes H or $CH_3$, $R_3$ denoting an alkyl radical containing from 12 to 22 carbon atoms, and
  a crosslinking agent, which is a well-known copolymerizable unsaturated polyethylenic monomer, for instance diallyl phthalate, allyl(meth)acrylate, divinylbenzene, (poly)ethylene glycol dimethacrylate and methylenebisacrylamide.

Among anionic associative polymers of this type that will be used more particularly are those consisting of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Mention may also be made of polymers which, besides the monomers of formula (II) and of formula (III), contain one or more other monomers. This additional monomer may especially be a vinyllactam and in particular vinylpyrrolidone.

An example of a polymer that may be mentioned is the acrylic acid/lauryl methacrylate/vinylpyrrolidone terpolymer sold under the name Acrylidone LM by the company ISP.

c) maleic anhydride/$C_{30}$-$C_{38}$ α-olefin/alkyl maleate anionic associative terpolymers, such as the product (maleic anhydride/$C_{30}$-$C_{38}$ α-olefin/isopropyl maleate copolymer) sold under the name Performa V 1608® by the company Newphase Technologies.

d) acrylic anionic associative terpolymers comprising:
  (i) 20% to 70% by weight of an α,β-monoethylenically unsaturated carboxylic acid,
  (ii) 20% to 80% by weight of a non-surfactant α,β-monoethylenically unsaturated monomer other than (i),
  (iii) 0.5% to 60% by weight of a nonionic monourethane, which is the product of reaction of a monohydric surfactant with a monoethylenically unsaturated monoisocyanate,
such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

e) anionic associative copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22® sold by the company Röhm & Haas, which is a methacrylic acid/ethyl acrylate/oxyalkylenated stearyl methacrylate terpolymer.

f) associative celluloses modified with groups comprising at least one fatty chain, such as alkyl, arylalkyl or alkylaryl groups comprising from 8 to 30 carbon atoms.

g) quaternized hydroxyethylcelluloses modified with groups comprising at least one fatty chain, such as alkyl, arylalkyl or alkylaryl groups comprising from 8 to 30 carbon atoms.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

h) the cationic polymer(s) obtained by polymerization of a monomer mixture comprising one or more vinyl monomers substituted with one or more amino groups, one or more hydrophobic nonionic vinyl monomers, and one or more associative vinyl monomers.

In particular, among these cationic polymers, mention may be made especially of the compound sold by the company Noveon under the name Aqua CC and which corresponds to the INCI name Polyacrylate-1 Crosspolymer.

Polyacrylate-1 Crosspolymer is the product of polymerization of a monomer mixture comprising:
  a di($C_1$-$C_4$ alkyl)amino($C_1$-$C_6$ alkyl) methacrylate,
  one or more $C_1$-$C_{30}$ alkyl esters of (meth)acrylic acid,
  a polyethoxylated $C_{10}$-$C_{30}$ alkyl methacrylate (20-25 mol of ethylene oxide units),
  a 30/5 polyethylene glycol/polypropylene glycol allyl ether,
  a hydroxy($C_2$-$C_6$ alkyl) methacrylate, and
  an ethylene glycol dimethacrylate.

i) amphoteric associative polymers prepared by copolymerizing:
1) at least one monomer of formula (Ibis) or (IIbis) below:

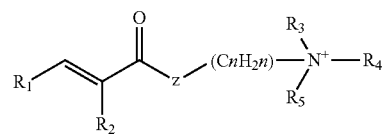

(Ibis)

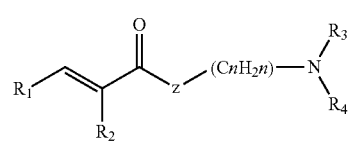

(IIbis)

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms,
Z represents an NH group or an oxygen atom,
n is an integer from 2 to 5,
$A^-$ is an anion derived from an organic or mineral acid, such as a methosulfate anion or a halide such as chloride or bromide;
2) at least one monomer of formula (IIIbis):

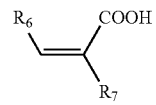

in which $R_6$ and $R_7$, which may be identical or different, represent a hydrogen atom or a methyl radical;
and
3) at least one monomer of formula (IVbis):

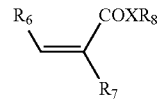

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;
at least one of the monomers of formula (Ibis), (IIbis) or (IIIbis) comprising at least one fatty chain containing 8 to 30 carbon atoms.

The monomers of formulae (Ibis) and (IIbis) of the present invention are preferably chosen from the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

More particularly, the monomer of formula (Ibis) is chosen from acrylamidopropyltrimethylammonium chloride and methacrylamidopropyltrimethylammonium chloride.

The monomers of formula (IIIbis) of the present invention are preferably chosen from the group consisting of acrylic acid, methacrylic acid, crotonic acid and 2-methylcrotonic acid. More particularly, the monomer of formula (VII) is acrylic acid.

The monomers of formula (IV) of the present invention are preferably chosen from the group formed by $C_{12}$-$C_{22}$ and more particularly $C_{16}$-$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (Ibis), (IIbis) or (IVbis)), and preferably from 1.5 mol % to 6 mol %.

The weight-average molecular weights of the amphoteric associative polymers according to the invention may range from 500 to 50 000 000 and are preferably between 10 000 and 5 000 000.

The amphoteric associative polymers according to the invention may also contain other monomers such as non-ionic monomers and in particular such as $C_1$-$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

j) nonionic associative celluloses modified with groups comprising at least one fatty chain containing 8 to 30 carbon atoms and preferably from 10 to 22 carbon atoms, such as alkyl, arylalkyl or alkylaryl groups, or mixtures thereof, and in which the alkyl groups are preferably $C_8$-$C_{22}$, for instance the product Natrosol Plus Grade 330 CS® ($C_{16}$ alkyls) sold by the company Aqualon, or the product Bermocoll EHM 100® sold by the company Berol Nobel.

Also suitable are those modified with alkylphenyl polyalkylene glycol ether groups, such as the product Amercell Polymer HM-1500® (polyethylene glycol (15) nonylphenyl ether) sold by the company Amerchol.

k) associative nonionic hydroxypropyl guars modified with groups comprising at least one fatty chain comprising from 8 to 30 carbon atoms and preferably from 10 to 22 carbon atoms, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhodia.

l) associative nonionic copolymers of vinylpyrrolidone and of fatty-chain hydrophobic monomers comprising from 8 to 30 carbon atoms and preferably from 10 to 22 carbon atoms, of which examples that may be mentioned include:
the products Antaron V216® or Ganex V216® (vinylpyrrolidone/hexadecene copolymer) sold by the company I.S.P.,
the products Antaron V220® or Ganex V220® (vinylpyrrolidone/eicosene copolymer) sold by the company I.S.P., m) associative nonionic copolymers of $C_1$-$C_6$ alkyl methacrylates or acrylates and of amphiphilic monomers comprising at least one fatty chain containing 8 to 30 carbon atoms and preferably from 10 to 22 carbon atoms, preferably oxyethylenated, for instance the oxyethylenated methyl acrylate/stearyl acrylate copolymer sold by the company Goldschmidt under the name Antil 208®.

n) associative nonionic copolymers of hydrophilic acrylates or methacrylates and of hydrophobic monomers comprising at least one fatty chain containing 8 to 30 carbon atoms and preferably from 10 to 22 carbon atoms, for instance the polyethylene glycol methacrylate/lauryl methacrylate copolymer.

o) associative nonionic polyurethane polyethers comprising in their chain both hydrophilic blocks, which are preferably polyoxyethylenated, and hydrophobic blocks which may be aliphatic sequences alone and/or cycloaliphatic and/or aromatic sequences comprising from 8 to 30 carbon atoms and preferably from 10 to 22 carbon atoms.

p) associative nonionic polymers with an aminoplast ether backbone bearing at least one fatty chain comprising from 8 to 30 carbon atoms and preferably from 10 to 22 carbon atoms, such as the Pure Thix® compounds sold by the company Sud-Chemie.

q) mixtures thereof.

Preferably, the thickening polymer(s) are chosen from nonionic, anionic and cationic polymers and even more preferentially from nonionic and cationic polymers.

In a preferred embodiment of the invention, the thickening polymer(s) are chosen from nonionic non-associative polymers and in particular from guar gums.

Advantageously, the content of thickening polymer ranges from 0.01% to 10% by weight, preferably from 0.1% to 5% by weight and better still from 0.2% to 3% by weight relative to the total weight of the composition.

Alkaline Agent

The composition according to the invention may optionally comprise at least one alkaline agent.

This agent may be chosen from mineral or organic or hybrid alkaline agents, or mixtures thereof.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the function of highest basicity.

Mention may be made, as hybrid compounds, of the salts of the abovementioned amines with acids, such as carbonic acid or hydrochloric acid.

The organic alkaline agent(s) are chosen, for example, from alkanolamines, oxyethylenated and/or oxypropylenated ethylenediamines, amino acids and the compounds having the formula below:

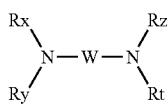

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for implementing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids can be in the neutral or ionic form.

Mention may in particular be made, as amino acids which can be used in the present invention, of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to the formula below:

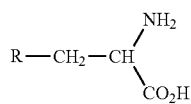

in which R denotes a group chosen from:

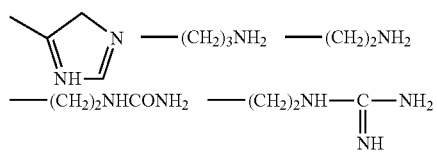

The compounds corresponding to the formula above are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine can also be chosen from amino acid dipeptides. As amino acid dipeptides that may be used in the present invention, mention may be made especially of carnosine, anserine and balenine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

As hybrid compounds, mention may be made in particular of guanidine carbonate or monoethanolamine hydrochloride.

According to one embodiment of the invention, the dye composition used in the process of the invention contains, as alkaline agent, aqueous ammonia and/or at least one alkanolamine and/or at least one basic amino acid, more advantageously aqueous ammonia and/or at least one alkanolamine.

Preferably, the alkaline agent is chosen from aqueous ammonia and monoethanolamine, or mixtures thereof.

Even more preferentially, the alkaline agent is an alkanolamine and better still is monoethanolamine.

Advantageously, the composition has a content of alkaline agent(s), and preferably of organic amine(s), when they are present, ranging from 0.01% to 30% by weight, preferably from 0.1% to 20% by weight and better still from 1% to 10% by weight, relative to the weight of the said composition. It should be noted that this content is expressed as $NH_3$ when the alkaline agent is aqueous ammonia.

Additives

The composition may also contain various adjuvants conventionally used in compositions for dyeing or lightening the hair, such as anionic or nonionic polymers, or mixtures thereof; cationic surfactants; antioxidants; penetrants; sequestrants; fragrances; dispersants; film-forming agents; ceramides; preserving agents; vitamins, opacifiers.

The above adjuvants are generally present in an amount, for each of them, of between 0.01% and 20% by weight relative to the weight of the composition.

In a specific embodiment, the composition of the invention contains at least one vitamin.

The vitamins that may be of use in the composition of the invention can in particular be chosen from vitamin C, A vitamins, B vitamins, D vitamins, vitamin E and vitamin F, and derivatives thereof.

Vitamin C

Vitamin C corresponds to ascorbic acid which is generally in L form, since it is usually extracted from natural products. Ascorbic acid derivatives are, more particularly, its salts, such as in particular sodium ascorbate, magnesium ascorbyl phosphate or sodium ascorbyl phosphate; it esters, for instance in particular its esters such as ascorbyl acetate, ascorbyl palmitate and ascorbyl propionate; its oxidized form, dehydroascorbic acid; or its sugars, such as in particular glycosylated ascorbic acid, and mixtures thereof.

Vitamin B3

Vitamin B3, also known as vitamin PP, is a compound of formula

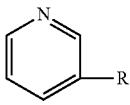

in which R can be —CONH₂ (niacinamide), —COOH (nicotinic acid or niacin), or CH₂OH (nicotinyl alcohol), —CO—NH—CH₂—COOH (nicotinuric acid) or —CO—NH—OH (niconityl hydroxamic acid).

As vitamin B3 derivatives, mention may, for example, be made of nicotinic acid esters such as tocopheryl nicotinate, amides derived from niacinamide by substitution of hydrogen groups of —CONH₂, products of reaction with carboxylic acids and amino acids, and esters of nicotinyl alcohol and of carboxylic acids such as acetic acid, salicylic acid, glycolic acid or palmitic acid. Mention may also be made of the following derivatives: 2-chloronicotinamide, 6-methylnicotinamide, 6-aminonicotinamide, N-methylnicotinamide, N,N-dimethylnicotinamide, N-(hydroxymethyl)nicotinamide, quinolinic acid imide, nicotinanilide, N-benzylnicotinamide, N-ethylnicotinamide, nifenazone, nicotinaldehyde, isonicotinic acid, methylisonicotinic acid, thionicotinamide, nialamide, 2-mercaptonicotinic acid, nicomol et niaprazine.

As other vitamin B3 derivatives, mention may also be made of its inorganic salts, such as chlorides, bromides, iodides or carbonates, and its organic salts, such as the salts obtained by reaction with carboxylic acids, such as acetate, salicylate, glycolate, lactate, malate, citrate, mandelate, tartrate, etc.

Vitamin B5

Vitamin B5 is pantothenic acid

As vitamin B5 derivatives, use may be made of panthenol or panthenyl alcohol or 2,4-dihydroxy-N-(3-hydroxypropyl)-3,3-dimethylbutanamide, in its various forms: D-panthenol, DL-panthenol which is the alcohol form of pantothenic acid and one of its precursors. Use may also be made, as derivatives, of calcium pantothenate, pantethine, pantotheine, panthenyl ethyl ether, pangamic acid, pyridoxine, pantoyl lactose, and natural compounds containing same, such as royal jelly.

Vitamin D

As vitamin D, mention may be made of vitamin D1 (lumisterol(1)/calciferol(1) complex), vitamin D2 (calciferol) and vitamin D3 (colecalciferol). By way of derivatives, mention may be made of vitamin D analogues such as those described in document WO-A-00/26167, for instance:

3-hydroxymethyl-5-{2-[3-(5-hydroxy-5- or 6-methylhexyl) phenyl]vinyl}phenol,
3-[3-(5-hydroxy-1,5-(dimethyl)hexyl)phenoxymethyl]-5-hydroxymethylphenol,
6-[3-(3,4-bis(hydroxymethyl)benzyloxy)phenyl]-2-methylhepta-3,5-dien-2-ol,
6-[3-(3,4-bis(hydroxymethyl)benzyloxy)phenyl]-2-methylhexan-2-ol,
6-[3-(3,4-bis(hydroxymethyl)phenoxymethyl)phenyl]-2-methylheptan-2-ol,
7-[3-(3,4-bis(hydroxymethyl)phenoxymethyl)phenyl]-3-ethyloctan-3-ol,
5-{2-[4-(5-hydroxy-5-methylhexyl)phenyl]-vinyl ou-ethyl}benzene-1,3-diol,
5-{2-[3- or 4-(6-hydroxy-6-methylheptyl)phenyl] vinyl}benzene-1,3-diol,
5-{2-[3- or 4-(6-hydroxy-6-methylheptyl)phenyl] ethyl}benzene-1,3-diol,
2-hydroxymethyl-4-{2-[3- or 4-(5-hydroxy-5-methylhexyl) phenyl]vinyl}phenol,
2-hydroxymethyl-4-{2-[3 or 4-(6-hydroxy-6-methylheptyl) phenyl]vinyl}phenol,
2-hydroxymethyl-4-{2-[3- or 4-(5-hydroxy-5-methylheptyl) phenyl]ethyl}phenol,
2-hydroxymethyl-4-{2-[3- or 4-(6-hydroxy-6-methylheptyl) phenyl]ethyl}phenol,
2-hydroxymethyl-5-{2-[4-(5-hydroxy-5-methylhexyl)phenyl]vinyl}phenol,
6-[3-(3,4-bis(hydroxymethyl)benzyloxy)phenyl]-2-methylheptan-2-ol,
4-[3-(5-hydroxy-1,5-(dimethyl)hexyl)phenoxymethyl]-2-hydroxymethylphenol,
6-{3- or 4-[2-(3,4-bis(hydroxymethyl)phenyl)vinyl]phenyl}-2-methylhexan-2-ol,
7-{4-[2-(3,4-bis(hydroxymethyl)phenyl)vinyl]phenyl}-2-methylheptan-2-ol,
5-{2-[3-(6-hydroxy-6-methylheptyl)phenyl]-1-methylvinyl}benzene-1,3-diol,
5-{2-[3-(5-hydroxy-5-methylhexyl)phenyl]vinyl}benzene-1,3-diol,
5-[3-(6-hydroxy-6-methylheptyl)phenoxymethyl]benzene-1,3-diol,
5-{2-[3-(7-hydroxy-7-methyloct-1-enyl)phenyl] vinyl}benzene-1,3-diol,
5-{2-[3-(7-hydroxy-7-methyloctyl)phenyl]vinyl}benzene-1,3-diol,
4-{2-[3-(6-hydroxy-6-methylheptyl)phenyl]vinyl}benzene-1,2-diol,
3-{2-[3-(6-hydroxy-6-methylheptyl)phenyl]vinyl}phenol,
6-{3-[2-(3,5-bis(hydroxymethyl)phenyl)vinyl]phenyl}-2-methylhexan-2-ol,
3-{2-[3-(7-hydroxy-7-methyloctyl)phenyl]vinyl}phenol,
7-{3-[2-(3,5-bis(hydroxymethyl)phenyl)vinyl]phenyl}-2-methylheptan-2-ol,
7-{3-[2-(3,4-bis(hydroxymethyl)phenyl)vinyl]phenyl}-2-methylheptan-2-ol,
7-{3-[2-(4-hydroxymethylphenyl)vinyl]phenyl}-2-methylheptan-2-ol,
4-{2-[3-(7-hydroxy-7-methyloct-1-enyl)phenyl] vinyl}benzene-1,2-diol,
7-[3-(3,4-bis(hydroxymethyl)phenylethynyl)phenyl]-2-methylheptan-2-ol,
5-{2-[3-(6-hydroxy-6-methylhept-1-enyl)phenyl] vinyl}benzene-1,3-diol,
5-{2-[3-(7-ethyl-7-hydroxynon-1-enyl)phenyl] vinyl}benzene-1,3-diol,
5-{2-[3-(7-hydroxy-1-methoxy-1,7-dimethyloctyl)phenyl] vinyl}benzene-1,3-diol,
5-{2-[3-(6-hydroxy-1-methoxy-1,6-dimethylheptyl)phenyl] vinyl}benzene-1,3-diol,
5-{2-[3-(5-hydroxypentyl)phenyl]vinyl}benzene-1,3-diol,
5-{2-[3-(5-hydroxy-6-methylheptyl)phenyl]vinyl}benzene-1,3-diol,
5-{2-[3-(6-hydroxy-7-methyloctyl)phenyl]vinyl}benzene-1,3-diol,
5-{2-[3-(5-hydroxy-6-methylhept-1-enyl)phenyl] vinyl}benzene-1,3-diol,
5-{2-[3-(6-hydroxy-7-methyloct-1-enyl)phenyl] vinyl}benzene-1,3-diol,
5-{2-[3-(1,6-dihydroxy-1,6-dimethylheptyl)phenyl] vinyl}benzene-1,3-diol,
5-{2-[3-(6-hydroxy-1,6-(dimethyl)hept-1-enyl)phenyl] vinyl}benzene-1,3-diol.

Vitamin F

Vitamin F is a mixture of essential fatty acids, i.e. of unsaturated acids which have at least one double bond, such as linoleic acid or 9,12-octadecadienoic acid and its stereoisomers, linolenic acid in α form (9,12,15-octadecatrienoic acid) or γ form (6,9,12-octadecatrienoic acid) and their stereoisomers, arachidonic acid or 5,8,11,14-eicosatetraenoic acid and its stereoisomers.

Vitamin F, or mixtures of unsaturated acids which have at least one double bond and in particular mixtures of linoleic acid, linolenic acid and arachidonic acid, or the compounds containing same, and in particular oils of vegetable origin containing same, for instance jojoba oil, can be used in the composition of the present invention.

Vitamin E

Vitamin E is alpha-tocopherol.

The vitamin E derivatives can be chosen from esters of vitamin E, and in particular the acetate, succinate or nicotinate.

The composition of the invention can comprise one or more vitamins, of the same category or of different categories.

Preferably, the vitamins are chosen from water-soluble vitamins and in particular vitamins B or C.

According to one particular embodiment, the composition comprises at least vitamin C in ascorbic acid form.

The vitamin(s) may be present in an amount ranging from 0.005% to 1% by weight, and preferably from 0.1% to 1% by weight, of active material relative to the total weight of the composition.

The composition according to the invention may comprise water and/or one or more organic solvents.

Examples of organic solvents that may be mentioned include linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol monomethyl, monoethyl or monobutyl ether, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The organic solvents, when they are present, generally represent between 1% and 40% by weight relative to the total weight of the dye composition, and preferably between 5% and 30% by weight relative to the total weight of the dye composition.

The composition is preferably aqueous.

In this case, it preferably comprises from 30% to 95% by weight of water, better still from 40% to 90% by weight of water and even better still from 50% to 85% by weight of water relative to the total weight of the composition.

The pH of the composition according to the invention, if it is aqueous, generally ranges from 6 to 12 and preferentially from 8.5 to 11.

It can be adjusted by adding acidifying agents, such as hydrochloric acid, (ortho)phosphoric acid, sulfuric acid, boric acid, and also carboxylic acids, for instance acetic acid, lactic acid or citric acid, or sulfonic acids. Alkaline agents such as those previously mentioned may also be used.

Dyeing Process

The composition described previously is applied to wet or dry keratin fibres, in the presence of at least one oxidizing agent other than atmospheric oxygen.

In particular, the oxidizing agent(s) suitable for use in the present invention are chosen, for example, from hydrogen peroxide, urea peroxide, alkali metal bromates or ferricyanides, peroxygenated salts, for instance persulfates, perborates, peracids and precursors thereof and percarbonates of alkali metals or alkaline-earth metals. Advantageously, the oxidizing agent is hydrogen peroxide.

The composition according to the invention, in the presence of the oxidizing agent, is usually left in place on the fibres for a time generally of from 1 minute to 1 hour and preferably from 5 minutes to 30 minutes.

The temperature during the dyeing process is conventionally between room temperature (between 15° C. and 25° C.) and 80° C. and preferably between room temperature and 60° C.

After the treatment, the human keratin fibres are advantageously rinsed with water. They can optionally be washed with a shampoo, followed by rinsing with water, before being dried or left to dry.

The composition applied in the process according to the invention is generally prepared extemporaneously before the application, by mixing at least two compositions.

In particular, composition (A) according to the invention free of oxidizing agent other than atmospheric oxygen and comprising at least one oxidation dye is mixed with a composition (B) comprising at least one oxidizing agent other than atmospheric oxygen.

Advantageously, compositions (A) and (B) are aqueous.

The term "aqueous composition" means a composition comprising at least 5% by weight of water relative to the weight of this formulation.

Preferably, an aqueous composition comprises more than 10% by weight of water and even more advantageously more than 20% by weight of water.

Advantageously, composition (A) is a direct emulsion (oil-in-water: O/W) or an inverse emulsion (water-in-oil: W/O), and preferably a direct emulsion (O/W).

More particularly, composition (A) comprises at least one basifying agent.

As regards composition (B) comprising the oxidizing agent as defined previously, it may also comprise one or more acidifying agents as indicated previously.

Usually, the pH of the oxidizing composition, when it is aqueous, is less than 7.

Preferably, the oxidizing composition comprises hydrogen peroxide as oxidizing agent, in aqueous solution, the concentration of which varies, more particularly, from 0.1% to 50%, more particularly between 0.5% and 20% and even more preferably between 1% and 15% by weight, relative to the weight of the oxidizing composition.

In accordance with a particular variant of the invention, composition (B) comprises at least one oil. Preferably, in the case of this variant, the oil content is at least 5% by weight, even more preferentially at least 10% by weight and better still at least 15% of fatty substances that are liquid at room temperature (25° C.), relative to the weight of this formulation.

According to another advantageous variant of the invention, composition (B) comprises at least one cationic polymer.

According to another advantageous variant of the invention, composition (B) comprises less than 7% of solid fatty alcohols.

Moreover, compositions (A) and (B) are preferably mixed together before use, in an (A)/(B) weight ratio ranging from 0.2 to 10 and better still from 0.5 to 2.

In addition, the composition used in the process according to the invention, i.e. the composition resulting from mixing together the two compositions (A) and (B), has a content of fatty substance other than solid fatty alcohols of at least 10% by weight, better still of at least 15% by weight and even better still of at least 20% by weight, relative to the weight of the composition resulting from mixing together the two abovementioned compositions.

Everything that has been described previously concerning the ingredients of the composition according to the invention remains valid in the case of compositions (A) and (B), the contents taking into account the degree of dilution during mixing.

The examples that follow serve to illustrate the invention without, however, being limiting in nature.

EXAMPLES

Example 1

The following compositions are prepared (the amounts are expressed in g % of active material):

Composition 1:

| | |
|---|---|
| Resorcinol | 0.5 |
| Ethanolamine | 5 |
| Sodium laureth sulfate containing 2.2 EO | 1.75 |
| Hydroxypropyl guar | 1 |
| Ascorbic acid | 0.5 |
| N,N-Bis(2-hydroxyethyl)-p-phenylenediamine sulfate | 0.073 |
| meta-Aminophenol | 0.18 |
| EDTA | 0.2 |
| 2-Methylresorcinol | 0.1 |
| PEG-40 hydrogenated castor oil | 1 |
| 2,4-Diaminophenoxyethanol hydrochloride | 0.019 |
| Sodium metabisulfite | 0.5 |
| Mineral oil | 60 |
| 2,5-Toluenediamine | 0.6732 |
| Water | qs 100 |

Composition 2:

| | |
|---|---|
| Tocopherol | 0.1 |
| Sodium stannate | 0.04 |
| Pentasodium pentetate | 0.06 |
| Glycerol | 0.5 |
| Cetearyl alcohol | 6 |
| Hydrogen peroxide | 6 |
| Tetrasodium pyrophosphate | 0.03 |
| Mineral oil | 20 |
| PEG-4 rapeseed acid amide | 1.19 |
| Steareth-20 | 5 |
| Phosphoric acid | qs pH 2.2 |
| Water | qs 100 |

Application Method:

The two compositions are mixed together at the time of use in the following proportions: 10 g of composition 1 with 15 g of composition 2.

The mixture thus obtained is readily applied to locks at a rate of 10 g of mixture per 1 g of hair, for 30 minutes at room temperature (20° C.).

The hair is then easily rinsed, then washed with a standard shampoo and dried.

A light chestnut colour is obtained.

Example 2

The following compositions are prepared (the amounts are expressed in g % of active material):

Composition 1:

| | |
|---|---|
| Resorcinol | 0.5 |
| Ethanolamine | 5 |
| Sodium laureth sulfate containing 2.2 EO | 1.75 |
| Hydroxypropyl guar | 1 |
| Ascorbic acid | 0.5 |
| N,N-Bis(2-hydroxyethyl)-p-phenylenediamine sulfate | 0.073 |
| meta-Aminophenol | 0.18 |
| EDTA | 0.2 |
| 2-Methylresorcinol | 0.1 |
| PEG-40 hydrogenated castor oil | 1 |
| 2,4-Diaminophenoxyethanol hydrochloride | 0.019 |
| Polysorbate 21 | 2 |
| Sodium metabisulfite | 0.5 |
| Mineral oil | 60 |
| 2,5-Toluenediamine | 0.673 |
| Water | qs 100 |

Composition 2:

| | |
|---|---|
| Tocopherol | 0.1 |
| Sodium stannate | 0.04 |
| Pentasodium pentetate | 0.06 |
| Glycerol | 0.5 |
| Cetearyl alcohol | 6 |
| Hydrogen peroxide | 6 |
| Tetrasodium pyrophosphate | 0.03 |
| Mineral oil | 20 |
| PEG-4 rapeseed acid amide | 1.19 |
| Steareth-20 | 5 |
| Phosphoric acid | qs pH 2.2 |
| Water | qs 100 |

Application Method:

The two compositions are mixed together at the time of use in the following proportions: 10 g of composition 1 with 15 g of composition 2.

The mixture thus obtained is readily applied to locks at a rate of 10 g of mixture per 1 g of hair, for 30 minutes at room temperature (20° C.).

The hair is then easily rinsed, then washed with a standard shampoo and dried.

A light chestnut colour is obtained.

The invention claimed is:

1. A composition for dyeing keratin fibers, comprising:
at least one oxidation dye precursor;
at least one ionic surfactant chosen from:
anionic surfactants chosen from $(C_{12}-C_{20})$ alkyl sulfates, $(C_{12}-C_{20})$ alkyl ether sulfates comprising from 2 to 20 ethylene oxide units, or mixtures thereof,
amphoteric or zwitterionic surfactants chosen from $(C_8-C_{20})$alkylbetaines, $(C_8-C_{20})$alkylamido $(C_3-C_8)$ alkylbetaines, or the compounds of formula (B'2):

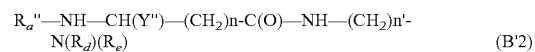

wherein:
Y" is chosen from the groups —C(O)OH, —C(O)OZ", —$CH_2$—CH(OH)—$SO_3$H, —$CH_2$—CH(OH)—$SO_3$—Z";
$R_d$ and $R_e$, independently of each other, are chosen from $C_1$-$C_4$ alkyl or hydroxyalkyl radical;
Z"" is chosen from a cationic counterion derived from an alkali metal or alkaline-earth metal, an ammonium ion or an ion derived from an organic amine;

$R_a''$ is chosen from a $C_{10}$-$C_{30}$ alkyl or alkenyl group of an acid $R_a''$—C(O)OH; and n and n', independently of each other, are integers ranging from 1 to 3, or mixtures thereof;

at least one oil, present in a concentration of about 10% to about 70% by weight, relative to the total weight of the composition;

optionally at least one solid fatty alcohol chosen from saturated linear alcohols comprising from 8 to 30 carbon atoms, present in an amount of up to about 0.5% by weight, relative to the weight of the composition; and at least one thickening polymer, wherein such composition is free of any oxidizing agent other than atmospheric oxygen and is in cream form.

2. The composition according to claim 1, wherein the at least one oxidation dye precursor is chosen from oxidation bases or salts thereof.

3. The composition according to claim 1, wherein the at least one oxidation dye precursor is chosen from couplers or the addition salts thereof with an acid.

4. The composition according to claim 1, wherein the at least one ionic surfactant is chosen from anionic surfactants chosen from ($C_{12}$-$C_{20}$) alkyl sulfates, ($C_{12}$-$C_{20}$) alkyl ether sulfates comprising from 2 to 20 ethylene oxide units, or mixtures thereof.

5. The composition according to claim 1, wherein the at least one ionic surfactant is chosen from amphoteric or zwitterionic surfactants chosen from cocamidopropylbetaine, cocoylbetaine, the sodium salt of diethylaminopropyl laurylaminosuccinamate, or mixtures thereof.

6. The composition according to claim 1, wherein the anionic surfactants are chosen from ($C_{12}$-$C_{20}$) alkyl sulfates, or ($C_{12}$-$C_{20}$) alkyl ether sulfates comprising from 2 to 20 ethylene oxide units in the form of alkali metal, ammonium, amino alcohol, alkaline-earth metal salts, or mixtures thereof.

7. The composition according to claim 1, further comprising at least one nonionic surfactant.

8. The composition according to claim 7, wherein the at least one nonionic surfactant is chosen from:

oxyalkylenated ($C_8$-$C_{24}$)alkylphenols;

saturated or unsaturated, linear or branched, oxyalkylenated or glycerolated $C_8$-$C_{30}$ alcohols;

saturated or unsaturated, linear or branched, oxyalkylenated $C_8$-$C_{30}$ amides;

saturated or unsaturated, linear or branched, $C_8$-$C_{30}$ acid esters of polyethylene glycols;

saturated or unsaturated, linear or branched, $C_8$-$C_{30}$ acid esters of sorbitol;

fatty acid esters of sucrose;

($C_8$-$C_{30}$)alkylpolyglycosides, ($C_8$-$C_{30}$)alkenylpolyglycosides, which are optionally oxyalkylenated (0 to 10 oxyalkylene units) and which comprise 1 to 15 glucose units, ($C_8$-$C_{30}$)alkylglucoside esters;

saturated or unsaturated, oxyethylenated plant oils;

condensates of ethylene oxide and/or of propylene oxide, alone or as mixtures;

N—($C_8$-$C_{30}$)alkylglucamine derivatives and N—($C_8$-$C_{30}$)acyl-methylglucamine derivatives;

aldobionamides;

amine oxides;

oxyethylenated and/or oxypropylenated silicones; or mixtures thereof.

9. The composition according to claim 1, wherein the at least one ionic surfactant is present in an amount ranging from about 0.1% to about 30% by weight, relative to the total weight of the composition.

10. The composition according to claim 1, wherein the at least one oil is chosen from mineral oils.

11. The composition according to claim 1, wherein the at least one thickening polymer is an ionic or nonionic non-associative polymer, or a nonionic, anionic, cationic or amphoteric associative polymer, or mixtures thereof; and can be chosen from:

Non-associative polymers chosen from:
a) crosslinked homopolymers or copolymers of acrylic or methacrylic acid,
b) crosslinked homopolymers of 2-acrylamido-2-methyl-propanesulfonic acid, and crosslinked acrylamide copolymers thereof,
c) ammonium acrylate homopolymers or copolymers of ammonium acrylate and of acrylamide,
d) nonionic guar gums,
e) biopolysaccharide gums of microbial origin, gums derived from plant exudates,
f) celluloses,
g) pectins and alginates, or
h) mixtures thereof; or Associative polymers chosen from:
aa) anionic associative polymers comprising at least one hydrophilic unit of the type such as an ethylenic unsaturated anionic monomer and at least one fatty-chain allyl ether unit comprising from 8 to 30 carbon atoms;
bb) anionic associative polymers comprising at least one hydrophilic unit of unsaturated olefinic carboxylic acid type and at least one hydrophobic unit of the type such as a ($C_{10}$-$C_{30}$)alkyl ester of an unsaturated carboxylic acid;
cc) maleic anhydride/$C_{30}$-$C_{38}$ α -olefin/alkyl maleate anionic associative terpolymers;
dd) acrylic anionic associative terpolymers comprising:
  (i) 20% to 70% by weight of an α, β-monoethylenically unsaturated carboxylic acid,
  (ii) 20% to 80% by weight of a non-surfactant αβ-monoethylenically unsaturated monomer other than (i),
  (iii) 0.5% to 60% by weight of a nonionic monourethane, which is the product of reaction of a monohydric surfactant with a monoethylenically unsaturated monoisocyanate,
ee) anionic associative copolymers comprising among their monomers an α, β-monoethylenically unsaturated carboxylic acid and an ester of an α, β-monoethylenically unsaturated carboxylic acid and of an oxyalkylenated fatty alcohol;
ff) associative celluloses modified with groups comprising at least one fatty chain comprising from 8 to 30 carbon atoms;
gg) quaternized hydroxyethylcelluloses modified with groups comprising at least one fatty chain comprising from 8 to 30 carbon atoms;
hh) the cationic polymer(s) obtained by polymerization of a monomer mixture comprising one or more vinyl monomers substituted with one or more amino groups, one or more hydrophobic nonionic vinyl monomers, and one or more associative vinyl monomers;
ii) amphoteric associative polymers prepared by copolymerizing:
  1) at least one monomer of formula (Ibis) or (IIbis) below:

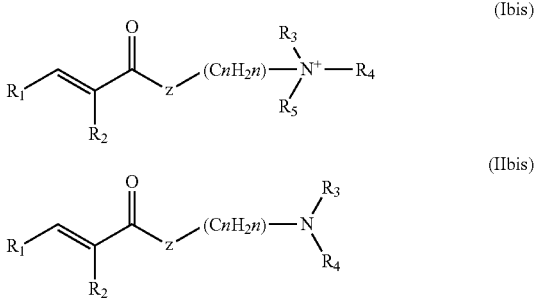
(Ibis)

(IIbis)

wherein $R_1$ and $R_2$, which may be identical or different, are chosen from a hydrogen atom and a methyl radical, $R_3$, $R_4$ and $R_5$, which may be identical or different, are chosen from a linear and branched alkyl radical containing from 1 to 30 carbon atoms, Z is chosen from an NH group and an oxygen atom, n is an integer from about 2 to about 5, 2) at least one monomer of formula (IIIbis):

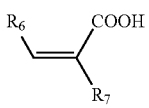

wherein $R_6$ and $R_7$, which may be identical or different, are chosen from a hydrogen atom or a methyl radical; and 3) at least one monomer of formula (IVbis):

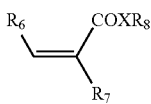

wherein $R_6$ and $R_7$, which may be identical or different, are chosen from a hydrogen atom and a methyl radical, X is chosen from an oxygen or nitrogen atom and $R_8$ is chosen from a linear or branched alkyl radical containing from 1 to 30 carbon atoms;

at least one of the monomers of formula (Ibis), (IIbis) or (IIIbis) comprising at least one fatty chain containing 8 to 30 carbon atoms;

jj) nonionic associative celluloses modified with groups comprising at least one fatty chain containing 8 to 30 carbon atoms, or modified with alkylphenyl polyalkylene glycol ether groups;

kk) associative nonionic hydroxypropyl guars modified with groups comprising at least one fatty chain comprising from 8 to 30 carbon atoms;

ll) associative nonionic copolymers of vinylpyrrolidone and of fatty-chain hydrophobic monomers comprising from 8 to 30 carbon atoms;

mm) associative nonionic copolymers of $C_1$-$C_6$ alkyl methacrylates or acrylates and of amphiphilic monomers comprising at least one fatty chain containing 8 to 30 carbon atoms;

nn) associative nonionic copolymers of hydrophilic acrylates or methacrylates and of hydrophobic monomers comprising at least one fatty chain containing 8 to 30 carbon atoms;

oo) associative nonionic polyurethane polyethers comprising in their chain both hydrophilic blocks and hydrophobic blocks which may be aliphatic sequences alone and/or cycloaliphatic and/or aromatic sequences comprising from 8 to 30 carbon atoms;

pp) associative nonionic polymers with an aminoplast ether backbone bearing at least one fatty chain comprising from 8 to 30 carbon atoms; or qq) mixtures thereof.

12. The composition according to claim 1, wherein the at least one thickening polymer is chosen from nonionic, anionic and cationic polymers.

13. The composition according to claim 1, wherein the at least one thickening polymer is present in an amount ranging from about 0.01% to about 10% by weight, relative to the total weight of the composition.

14. The composition according to claim 1, wherein the composition does not comprise any solid fatty alcohol.

15. A process for dyeing keratin fibers, comprising:
(a) preparing a cosmetic mixture by mixing:
a dye composition comprising:
at least one oxidation dye precursor, at least one ionic surfactant chosen from:
anionic surfactants chosen from ($C_{12}$-$C_{20}$) alkyl sulfates, ($C_{12}$-$C_{20}$) alkyl ether sulfates comprising from 2 to 20 ethylene oxide units, or mixtures thereof,
amphoteric or zwitterionic surfactants chosen from ($C_8$-$C_{20}$)alkylbetaines, ($C_8$-$C_{20}$)alkylamido($C_3$-$C_8$) alkylbetaines, or the compounds of formula (B'2):

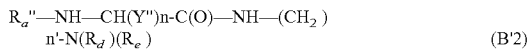

wherein:
Y" is chosen from the groups —C(O)OH, —C(O)OZ", —CH$_2$—CH(OH)—SO$_3$H, —CH$_2$—CH(OH)—SO$_3$—Z";
$R_d$ and $R_e$, independently of each other, are chosen from $C_1$-$C_4$ alkyl or hydroxyalkyl radical;
Z" is chosen from a cationic counterion derived from an alkali metal or alkaline-earth metal, an ammonium ion or an ion derived from an organic amine;
$R_a$" is chosen from a $C_{10}$-$C_{30}$ alkyl or alkenyl group of an acid $R_a$"—C(O)OH; and
n and n', independently of each other, are integers ranging from 1 to 3, or
mixtures thereof,
at least one oil, optionally at least one solid fatty alcohol present in an amount not more than about 0.5% by weight, relative to the weight of the composition, and at least one thickening polymer;
wherein such composition is free of any oxidizing agent other than atmospheric oxygen and is in cream form; and
an oxidizing composition comprising at least one oxidizing agent other than atmospheric oxygen; and
(b) applying said mixture to said keratin fibers.

16. A device for mixing and using a composition for dyeing keratin fibers, comprising:
a first compartment containing a dye composition comprising at least one oxidation dye precursor, at least one ionic surfactant chosen from:
anionic surfactants chosen from ($C_{12}$-$C_{20}$) alkyl sulfates, ($C_{12}$-$C_{20}$) alkyl ether sulfates comprising from 2 to 20 ethylene oxide units, or mixtures thereof, amphoteric or zwitterionic surfactants chosen from ($C_8$-$C_{20}$) alkylbetaines, ($C_8$-$C_{20}$)alkylamido($C_3$-$C_8$) alkylbetaines, or the compounds of formula (B'2):

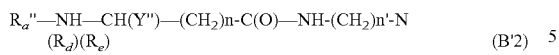
$$R_a''-NH-CH(Y'')-(CH_2)n-C(O)-NH-(CH_2)n'-N(R_d)(R_e) \quad (B'2)$$

wherein:
- Y" is chosen from the groups —C(O)OH, —C(O)OZ", —$CH_2$—CH(OH)—$SO_3$H, —$CH_2$—CH(OH)—$SO_3$—Z";
- $R_d$ and $R_e$t, independently of each other, are chosen from $C_1$-$C_4$ alkyl or hydroxyalkyl radical;
- Z" is chosen from a cationic counterion derived from an alkali metal or alkaline-earth metal, an ammonium ion or an ion derived from an organic amine;
- $R_a$" is chosen from a $C_{10}$-$C_{30}$ alkyl or alkenyl group of an acid $R_a$"—C(O)OH; and
- n and n', independently of each other, are integers ranging from 1 to 3, or
  mixtures thereof,
   at least one oil, optionally at least one solid fatty alcohol present in an amount not more than about 0.5% by weight, relative to the weight of the composition, and at least one thickening polymer; wherein such composition is free of any oxidizing agent other than atmospheric oxygen and is in cream form; and
- a second compartment containing an oxidizing composition comprising at least one oxidizing agent other than atmospheric oxygen.

* * * * *

UNITED STATES PATENT AND TRADEMARK OFFICE
CERTIFICATE OF CORRECTION

PATENT NO. : 10,201,483 B2
APPLICATION NO. : 14/418746
DATED : February 12, 2019
INVENTOR(S) : Delphine Charrier et al.

Page 1 of 1

It is certified that error appears in the above-identified patent and that said Letters Patent is hereby corrected as shown below:

In the Claims

Column 34, Line 34, please change "CH(Y")n" to -- CH(Y")-(CH2)n --.

Signed and Sealed this
Twenty-third Day of April, 2019

Andrei Iancu
*Director of the United States Patent and Trademark Office*